US011919924B1

(12) United States Patent
Sutter et al.

(10) Patent No.: US 11,919,924 B1
(45) Date of Patent: Mar. 5, 2024

(54) METHODS OF PURIFYING AND PRODUCING AN ADALIMUMAB ANTIBODY

(71) Applicant: Fresenius Kabi Deutschland GmbH, Bad Homburg (DE)

(72) Inventors: Harry-James Sutter, Vevey (CH); Matteo Costioli, Lausanne (CH); Hervé Broly, Chatel-St Denis (CH)

(73) Assignee: FRESENIUS KABI DEUTSCHLAND GMBH, Bad Homburg (DE)

(*) Notice: Subject to any disclaimer, the term of this patent is extended or adjusted under 35 U.S.C. 154(b) by 58 days.

(21) Appl. No.: 16/227,489

(22) Filed: Dec. 20, 2018

Related U.S. Application Data (63) Continuation of application No. 15/457,531, filed on Mar. 13, 2017, now abandoned.

(60) Provisional application No. 62/308,589, filed on Mar. 15, 2016.

(51) Int. Cl.
| | | |
|---|---|---|
| *C07K 1/18* | (2006.01) | |
| *A61K 39/395* | (2006.01) | |
| *B01D 15/38* | (2006.01) | |
| *B01J 20/04* | (2006.01) | |
| *C07K 1/20* | (2006.01) | |
| *C07K 16/24* | (2006.01) | |

(52) U.S. Cl.
CPC .......... *C07K 1/18* (2013.01); *A61K 39/39591* (2013.01); *B01D 15/3847* (2013.01); *B01J 20/048* (2013.01); *C07K 1/20* (2013.01); *C07K 16/241* (2013.01)

(58) Field of Classification Search
None
See application file for complete search history.

(56) References Cited

U.S. PATENT DOCUMENTS

| | | | | |
|---|---|---|---|---|
| 6,090,382 A | * | 7/2000 | Salfeld | A61P 31/12 424/133.1 |
| 2010/0234577 A1 | * | 9/2010 | Mazzola | C07K 1/18 530/388.1 |

FOREIGN PATENT DOCUMENTS

| | | | | |
|---|---|---|---|---|
| WO | WO 2005044856 | * | 5/2005 | C07K 16/06 |

OTHER PUBLICATIONS

Cummings et al. Monoclonal antibody purification by ceramic hydroxyapatite chromatography. Methods Mol Biol. 2014; 1131:241-51. (Year: 2014).*

(Continued)

*Primary Examiner* — Michelle S Horning
(74) *Attorney, Agent, or Firm* — Fox Rothschild LLP (57) ABSTRACT

The present invention relates to a method for purifying adalimumab or a biosimilar thereof from a sample comprising adalimumab or a biosimilar thereof and impurities, through the use of hydroxyapatite resin in a Bind/Elute (B/E) mode under conditions such that the adalimumab or a biosimilar thereof binds to the resin and at least a portion of the impurities remain unbound. The invention is also concerned with a pharmaceutical compositions=of the purified adalimumab or a biosimilar thereof, and adalimumab or a biosimilar thereof obtainable by the process of the invention.

13 Claims, 5 Drawing Sheets

Specification includes a Sequence Listing.

(56) References Cited

OTHER PUBLICATIONS

Gagnon. Monoclonal antibody purification with hydroxyapatite. New Biotechnology. vol. 25, No. 5, 287-293. (Year: 2009).*
Baker et al., Protein Structure Predication and Structural Genomics, Science (2001) vol. 294, No. 5540, pp. 93-96 (Year: 2001).*
Attwood, T. The Babel of Bioinformatics, Science (2000) vol. 290, No. 5491, pp. 471-473 (Year: 2000).*

* cited by examiner

RELATIVE LEVELS OF HMW AND LMW

SEQUENCE LISTING

```
<160> NUMBER OF SEQ ID NOS: 10

<210> SEQ ID NO 1
<211> LENGTH: 107
<212> TYPE: PRT
<213> ORGANISM: Artificial Sequence
<220> FEATURE:
<223> OTHER INFORMATION: adalimumab light chain variable region

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: adalimumab heavy chain variabe region

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45
```

```
Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 9
<212> TYPE: PRT
<213> ORGANISM: Artificial Sequence
<220> FEATURE:
<223> OTHER INFORMATION: adalimumab light chain variable region CDR3
<220> FEATURE:
<221> NAME/KEY: misc_feature
<222> LOCATION: (9)..(9)
<223> OTHER INFORMATION: Xaa can be any naturally occurring amino acid

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: adalimumab heavy chain variable region CDR3
<220> FEATURE:
<221> NAME/KEY: misc_feature
<222> LOCATION: (12)..(12)
<223> OTHER INFORMATION: Xaa can be any naturally occurring amino acid

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: adalimumab light chain variable region CDR2

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: adalimumab heavy chain variable region CDR2

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
```

```
<211> LENGTH: 11
<212> TYPE: PRT
<213> ORGANISM: Artificial Sequence
<220> FEATURE:
<223> OTHER INFORMATION: adalimumab light chain variable region CDR1

<400> SEQUENCE: 7

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial Sequence
<220> FEATURE:
<223> OTHER INFORMATION: adalimumab heavy chain variable region CDR1

<400> SEQUENCE: 8

Asp Tyr Ala Met His
1               5

<210> SEQ ID NO 9
<211> LENGTH: 321
<212> TYPE: DNA
<213> ORGANISM: Artificial Sequence
<220> FEATURE:
<223> OTHER INFORMATION: adalimumab light chain variable region

<400> SEQUENCE: 9
gacatccaga tgacccagtc tccatcctcc ctgtctgcat ctgtagggga cagagtcacc      60
atcacttgtc gggcaagtca gggcatcaga aattacttag cctggtatca gcaaaaacca     120
gggaaagccc ctaagctcct gatctatgct gcatccactt tgcaatcagg ggtcccatct     180
cggttcagtg gcagtggatc tgggacagat ttcactctca ccatcagcag cctacagcct     240
gaagatgttg caacttatta ctgtcaaagg tataaccgtg caccgtatac ttttggccag     300
gggaccaagg tggaaatcaa a                                               321

<210> SEQ ID NO 10
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 10
gaggtgcagc tggtggagtc tgggggaggc ttggtacagc ccggcaggtc cctgagactc      60
tcctgtgcgg cctctggatt cacctttgat gattatgcca tgcactgggt ccggcaagct     120
ccagggaagg gcctggaatg ggtctcagct atcacttgga atagtggtca catagactat     180
gcggactctg tgagggccg attcaccatc tccagagaca acgccaagaa ctccctgtat     240
ctgcaaatga acagtctgag agctgaggat acggccgtat attactgtgc gaaagtctcg     300
taccttagca ccgcgtcctc ccttgactat tggggccaag gtaccctggt caccgtctcg     360
agt                                                                  363
```

METHODS OF PURIFYING AND PRODUCING AN ADALIMUMAB ANTIBODY

BACKGROUND OF THE INVENTION

When a protein is produced for pharmacological use, it is important to remove impurities which may be toxic or result in adverse immunological responses in the patient. Such impurities include host cell proteins, nucleic acid molecules, lipids, polysaccharides as well as fragments and aggregates of the therapeutic molecule itself.

It is also important to recover a high proportion of any protein whether it has been subjected to a previous purification step (such as anionic or cationic exchange chromatography, Protein A purification) prior to the hydroxyapatite resin purification step of the present invention or whether the hydroxyapatite resin purification step is the first purification step following the end of the cell culture phase. Cell culture processes are highly regulated, monitored, and adjusted in order to ensure that the therapeutic antibody being produced is of high quality and also that the titre of the product is acceptable. Therefore, any subsequent purification steps must also retain this high yield and quality of protein to render the whole process effective and efficient.

The removal of aggregates (high molecular weight (HMW) species) is also very important. Antibody preparations harvested from cell lines often contain aggregates of the antibody that is produced by the cell line. The formation of the aggregates can adversely affect product safety. Aggregates may have implications in further manufacturing processes.

Removal of fragments (low molecular weight (LMW) species) of an antibody is also important as they may have serious safety implications if included at too high a level in the final therapeutic product.

SUMMARY OF THE INVENTION

The present invention provides a method of purifying an antibody having (i) a light chain sequence having at least 90% identity with SEQ ID NO:1 and a heavy chain sequence having at least 90% identity with SEQ ID NO:2; (ii) a light chain sequence having at least 95% identity with SEQ ID NO:1 and a heavy chain sequence having at 35 least 95% identity with SEQ ID NO:2; (iii) a light chain sequence of SEQ ID NO:1 and a heavy chain sequence of SEQ ID NO:2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine, the method comprising: a) contacting the sample with a hydroxyapatite resin under conditions such that the antibody binds to the resin and at least a portion of the impurities remain unbound to the resin; b) washing the resin with a wash buffer under conditions such that at least a portion of the impurities are separated from the antibody; and c) eluting the antibody from the resin under conditions such the antibody becomes unbound from the resin to produce an eluate wherein the eluate contains a lower level of impurities than the sample of step (a).

In embodiments of the present invention, the antibody is adalimumab or a biosimilar of adalimumab. In embodiments of the present invention, the antibody has a light chain sequence comprising SEQ ID NO: 3, SEQ ID NO: 5, and SEQ ID NO:7; and the antibody has a heavy chain sequence comprising SEQ ID NO: 4, SEQ ID NO:6, and SEQ ID NO: 8. In embodiments of the present invention, Xaa of SEQ ID NO:3 maybe any naturally occurring amino acid and preferably is Thr or Ala and Xaa of SEQ ID NO: 4 maybe any naturally occurring amino acid and preferably is Tyr or Asn.

In embodiments of the present invention, the conditions are such that the antibody binds to the resin comprise the use of a loading buffer, wherein the loading buffer: (i) has a pH of from about pH 6.0 to about pH 8.0; and (ii) comprises from about 2.5 mM to about 7.5 mM NaPO4. In embodiments of the present invention, the conditions are such that the antibody binds to the resin comprise the use of a loading buffer, wherein the loading buffer: (i) has a pH of about pH 7.5; and (ii) comprises about 5 mM NaPO4. In embodiments of the present invention, the conditions are such that the antibody becomes unbound from the resin comprise the use of an elution buffer, wherein the elution buffer: (i) has a pH of about pH 6.0 to about pH 8.0; (ii) comprises from about 5 mM to about 15 mM NaPO4; and (iii) comprises from about 300 mM to about 400 mM NaCl. In embodiments of the present invention, the conditions are such that the antibody becomes unbound from the resin comprise the use of an elution buffer, wherein the elution buffer: (i) has a pH of about pH 7.5; (ii) comprises about 10 mM NaPO4; and (iii) comprises about 350 mM NaCl.

In embodiments of the present invention, the impurities comprise one or more of host cell proteins, nucleic acid molecules, lipids, polysaccharides. In embodiments of the present invention, the impurities comprise aggregates of the antibody or fragments of adalimumab or mixtures thereof. In embodiments of the present invention, about 25 mg to about 40 mg of the antibody per litre of resin binds to the resin in step (a). In embodiments of the present invention, about 32 mg of the antibody per litre of resin is contacted with the resin. In embodiments of the present invention, the hydroxyapatite resin is CHT ceramic hydroxyapatite, type I, 40 μm. In embodiments of the present invention, the resin has a bed height from about 10 cm to about 16 cm.

In embodiments of the present invention, the method is carried out at about 15-25° C. In embodiments of the present invention, the eluate of step c) comprises aggregates at a level of at least 70%, preferably 75%, lower than the level of aggregates in the sample of step (a).

The present invention also provides a method of producing an antibody having (i) a light chain sequence having at least 90% identity with SEQ ID NO:1 and a heavy chain sequence having at least 90% identity with SEQ ID NO:2; (ii) a light chain sequence having at least 95% identity with SEQ ID NO:1 and a heavy chain sequence having at least 95% identity with SEQ ID NO:2; (iii) a light chain sequence of SEQ ID NO:1 and a heavy chain sequence of SEQ ID NO:2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine, comprising the steps of: a) expressing the antibody in CHO cells and secreting the antibody into a cell culture media to obtain a sample; b) contacting the antibody with a hydroxyapatite resin under conditions such that the antibody binds to the resin and at least a portion of the impurities remain unbound to the resin; c) washing the resin with a wash buffer under conditions such that at least a portion of the impurities are separated from the antibody; and d) eluting the antibody from the resin under conditions such the antibody becomes unbound from the resin to produce an eluate, wherein the eluate contains a lower level of impurities than the sample of step (a).

The present invention also provides an antibody obtained by any one of the above mentioned methods.

The present invention also provides a pharmaceutical composition comprising the above antibodies.

DETAILED DESCRIPTION

Hydroxyapatite (HA) chromatography uses insoluble hydroxylated calcium phosphate $(Ca_{10}(PO_4)_6(OH)_2$, which forms a matrix and a ligand as a solid phase chromatographic support that employs multiple chemical mechanisms to adsorb proteins and other solutes. Hydroxyapatite chromatography is described as a mixed mode ion exchange because it involves non-specific interactions between the positively charged calcium ions and the negatively charged phosphate ions on the HA resin with the negatively charged carboxyl groups of the proteins and the positively charged amino groups of the proteins, respectively. Due to the non-specific interactions involved, unlike anionic exchange or cationic exchange, it can be very difficult to predict the effectiveness of hydroxyapatite chromatography based on the physical and chemical properties of the protein (such as a therapeutic antibody) to be purified. Therefore, the particular loading buffer, elution conditions, and load and flow values cannot be easily predicted and must be very carefully elucidated to ensure sufficient removal of impurities, including HMW aggregates and LMW fragments whilst maintaining the recovery of a high yield of the protein (such as a therapeutic antibody).

As used herein, the term "aggregate" or "aggregates" refers to one or more products of agglomeration or oligomerisation of two or more individual molecules e.g. antibodies, including but not limited to dimers, trimers, tetramers, oligomers and other high molecular weight species which the skilled person would understand should not be included in the final purified antibody composition.

Generally, HA chromatography is carried out in a column format, as is known in the art.

The terms "resin" and "HA resin" as used herein refer to a hydroxyapatite solid phase which separates a protein, such as an antibody, from other molecules in a sample as result of differences in rates and conditions at which the individual molecules migrate through the hydroxyapatite solid phase and are used interchangeably herein.

Usually, the resin is equilibrated and a sample, containing a therapeutic antibody, is applied to the resin in a loading buffer following which a wash buffer is applied to wash out the impurities. The loading buffer ensures that the conditions are such that the antibody binds to the hydroxyapatite resin, and that at least a portion of the impurities (from which the antibody is to be separated) do not bind to the resin. It must be said that at least a portion of the impurities bonds stronger to the resin than the product of interest and will be washed out after the elution of the purified antibody. This second portion of impurities will only be uncoupled from the resin with high phosphate buffer (0.4-0.5 M PO4).

Therefore, the present invention provides a method of purifying an antibody having (i) a light chain sequence having at least 90% identity with SEQ ID NO:1 and a heavy chain sequence having at least 90% identity with SEQ ID NO:2; (ii) a light chain sequence having at least 95% identity with SEQ ID NO:1 and a heavy chain sequence having at least 95% identity with SEQ ID NO:2; (iii) a light chain sequence of SEQ ID NO:1 and a heavy chain sequence of SEQ ID NO:2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.from a sample comprising the antibody and impurities, the method comprising: a) contacting the sample with a hydroxyapatite resin under conditions such that the antibody binds to the resin and at least a portion of the impurities remain unbound to the resin; b) washing the resin with a wash buffer under conditions such that at least a portion of the impurities are separated from the antibody; and c) eluting the antibody from the resin under conditions such that the antibody becomes unbound from the resin to produce an eluate, wherein the eluate contains a lower level of impurities than the sample of step a).

As described below the antibody may also be adalimumab or a biosimilar thereof. In embodiments of the present invention, the antibody has a light chain sequence comprising SEQ ID NO: 3, SEQ ID NO: 5, and SEQ ID NO: 7; and the antibody has a heavy chain sequence comprising SEQ ID NO: 4, SEQ ID NO: 6, and SEQ ID NO: 8. In embodiments of the present invention, the antibody has a light chain sequence comprising SEQ ID NO: 3, wherein Xaa is any naturally occurring amino acid; and has a heavy chain sequence comprising SEQ ID NO: 4, wherein Xaa is any naturally occurring amino acid. In embodiments of the present invention, Xaa of SEQ ID NO: 3 is Threonine or Alanine. In embodiments of the present invention, Xaa of SEQ ID NO: 4 is Tyrosine or Asparagine.

The conditions of step (a) such that the antibody binds to the resin, may comprise the use of a loading buffer comprising a pH of about 6.0 to about 8.0, about 2.5 to about 7.5 mM NaPO4; and preferably comprising a pH of about 7.5 and about 5 mM NaPO4.

The conditions of step (c) such that the antibody becomes unbound from the resin may comprise the use of an HA elution buffer comprising a pH of about 6.0 to about 8.0, about 5 mM to about 15 mM NaPO4, and about 300 mM to about 400 mM NaCl; and preferably comprising a pH of about 7.5, about 10 mM NaPO4, and about 350 mM NaCl.

The impurities from which the antibody is separated may comprise one or more of host cell proteins, nucleic acid molecules, lipids, and polysaccharides.

The impurities may also include aggregates, fragments of the antibody, or mixtures thereof.

In the method of the invention, the sample may be contacted with the resin such that about 25 to about 40 mg of the antibody per litre of HA resin may be contacted with the resin. Preferably, no more than about 32 mg of the antibody per litre of resin is contacted with the resin.

The hydroxyapatite resin may be CHT ceramic hydroxyapatite, type I, 40 μm (BioRad, Hercules, California), or equivalents thereof, and/or the HA column may have a bed height may be from about 10 to about 16 cm. The method may be carried out at room temperature, from about 15-25° C., preferably 18° C. to about 22° C.

The eluate produced by step (c) may contain aggregates at a level of at least 75% lower, preferably at least 90% lower than the level of aggregates in the sample of step (a).

The eluate of step (c) may contain fragments at a level of at least 70% lower, preferably at least 80% lower than the level of fragments in the sample of step (a).

The antibody may be produced by expression in a cell culture, preferably in eukaryotic cells, more preferably in mammalian cells, and most preferably in Chinese hamster ovary (CHO) cells in a fed-batch culture prior to purification.

The invention also provides a method of producing an antibody having (i) a light chain sequence having at least 90% identity with SEQ ID NO:1 and a heavy chain sequence having at least 90% identity with SEQ ID NO:2, or (ii) a light chain sequence having at least 95% identity with SEQ ID NO:1 and a heavy chain sequence having at least 95% identity with SEQ ID NO:2, or (iii) a light chain sequence of SEQ ID NO:1 and a heavy chain sequence of SEQ ID NO:2, comprising the steps of: a) expressing the antibody in CHO cells and secreting the antibody into a cell culture media to obtain a sample; b) contacting the antibody with a hydroxyapatite resin under conditions such that the antibody binds to the resin and at least a portion of the impurities remain unbound to the resin; c) washing the resin with a wash buffer under conditions such that at least a portion of the impurities are separated from the antibody; and d) eluting the antibody from the resin under conditions such that the antibody becomes unbound from the resin to produce an eluate, wherein the eluate contains a lower level of impurities than the sample of step (a).

As described below the antibody may also be adalimumab or a biosimilar thereof. In embodiments of the present invention, the antibody has a light chain sequence comprising SEQ ID NO: 3, SEQ ID NO: 5, and SEQ ID NO: 7; and the antibody has a heavy chain sequence comprising SEQ ID NO: 4, SEQ ID NO: 6, and SEQ ID NO: 8. In embodiments of the present invention, the antibody has a light chain sequence comprising SEQ ID NO: 3, wherein Xaa is any naturally occurring amino acid; and has a heavy chain sequence comprising SEQ ID NO: 4, wherein Xaa is any naturally occurring amino acid. In embodiments of the present invention, Xaa of SEQ ID NO: 3 is Threonine or Alanine. In embodiments of the present invention, Xaa of SEQ ID NO: 4 is Tyrosine or Asparagine.

The invention also provides an antibody obtained by the process of the invention and a pharmaceutical composition comprising the antibody.

As used herein, the term "about" or "approximately" has its general meaning as understood to one of skill in the art within the context of the referenced value or range. In some embodiments, as understood to one of skill in the art, the term "about" or "approximately" means within 20%, 15%, 10%, 9%, 8%, 7%, 6%, 5%, 4%, 3%, 2%, 1%, 0.5% or 0.05% of a given value or range. about The term "antibody" is used as understood in the art, i.e. an immunoglobulin molecule that recognises and specifically binds to a target (such as a protein, polypeptide, peptide, carbohydrate, polynucleotide, lipid, or combinations of the foregoing) through at least one antigen recognition site within the variable region of the immunoglobulin molecule. In embodiments of the present invention, the antibody has (i) a light chain sequence having at least 90% identity with SEQ ID NO:1 and a heavy chain sequence having at least 90% identity with SEQ ID NO:2, or (ii) a light chain sequence having at least 95% identity with SEQ ID NO:1 and a heavy chain sequence having at least 95% identity with SEQ ID NO:2, or (iii) a light chain sequence of SEQ ID NO:1 and a heavy chain sequence of SEQ ID NO:2. In embodiments of the present invention, the antibody is adalimumab. In embodiments of the present invention, the antibody is a biosimilar of adalimumab. In embodiments of the present invention, the antibody has a light chain sequence comprising SEQ ID NO: 3, SEQ ID NO: 5, and SEQ ID NO: 7; and the antibody has a heavy chain sequence comprising SEQ ID NO: 4, SEQ ID NO: 6, and SEQ ID NO: 8. In embodiments of the present invention, the antibody has a light chain sequence comprising SEQ ID NO: 3, wherein Xaa is any naturally occurring amino acid; and has a heavy chain sequence comprising SEQ ID NO: 4, wherein Xaa is any naturally occurring amino acid. In embodiments of the present invention, Xaa of SEQ ID NO: 3 is Threonine or Alanine. In embodiments of the present invention, Xaa of SEQ ID NO: 4 is Tyrosine or Asparagine.

As used herein, "adalimumab" refers to any human monoclonal antibody that specifically binds a tumour-necrosis factor (TNF)-α, having the light chain sequence of SEQ ID NO:1 and the heavy chain sequence of SEQ ID NO:2. Adalimumab is sold under the trade name HUMIRA® and has CAS designation 33-1731-18-1.

As used herein, "biosimilar" (of an approved reference product/biological drug, such as a protein therapeutic, antibody, etc.) refers to a biologic product that is highly similar to a reference product notwithstanding minor differences in clinically inactive components having no clinically meaningful differences between the biological product and the reference product in terms of the safety, purity, and potency of the product. In one embodiment, the biosimilar biological product is biosimilar to the reference product based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is licensed and intended to be used and for which licensure is sought for the biological product. In one embodiment, the biosimilar biological product and reference product utilize the same mechanism or mechanisms of action for the condition or conditions of use prescribed, recommended, or suggested in the proposed labeling, but only to the extent the mechanism or mechanisms of action are known for the reference product. In one embodiment, the condition or conditions of use prescribed, recommended, or suggested in the labeling proposed for the biological product have been previously approved for the reference product. In one embodiment, the route of administration, the dosage form, and/or the strength of the biological product are the same as those of the reference product. In one embodiment, the facility in which the biological product is manufactured, processed, packed, or held meets standards designed to assure that the biological product continues to be safe, pure, and potent. The reference product may be approved in at least one of the U.S., Europe, or Japan.

The terms "culture" and "cell culture" as used herein refer to a eukaryotic cell population that is suspended in a medium under conditions suitable to survival and/or growth of the cell population. These terms may refer to the combination comprising the mammalian cell population and the medium in which the population is suspended.

The term "fed-batch culture" as used herein refers to a method of culturing cells in which additional components are provided to the culture at some time subsequent to the beginning of the culture process i.e. after day zero (0). The provided components typically comprise nutritional supplements for the cells which have been depleted during the culturing process. A fed-batch culture is typically stopped at some point and the cells and/or components in the medium are harvested and then purified.

The term "expression" or "expresses" are used herein to refer to transcription and translation occurring within a host cell. Protein encoded by a product gene can be quantitated either by assaying for the biological activity of the protein or by employing assays that are independent of such activity, such as western blotting or radioimmunoassay using antibodies that are capable of reacting with the protein. Sambrook et al., Molecular Cloning: A Laboratory Manual, pp. 18.1-18.88 (Cold Spring Harbor Laboratory Press, 1989).

The terms "medium", "cell culture medium" and "culture medium" as used herein refer to a solution containing nutrients which nourish growing eukaryotic cells. Typically, these solutions provide essential and non-essential amino acids, vitamins, energy sources, lipids, and trace elements required by the cell for minimal growth and/or survival. The solution may also contain components that enhance growth and/or survival above the minimal rate, including hormones and growth factors. The solution is preferably formulated to a pH and salt concentration optimal for cell survival and proliferation. The medium may also be a "defined medium" such as a serum-free medium and/or protein free medium that contains no proteins, hydrolysates or components of unknown composition. Defined media are free of animal-derived components and all components have a known chemical structure.

The term "titre" as used herein refers to the total amount of recombinantly expressed polypeptide or protein produced by a mammalian cell culture divided by a given amount of medium volume. Titre is typically expressed in units of milligrams of polypeptide or protein per milliliter of medium.

As used herein, the singular forms "a", "an", and "the" include plural forms unless the context clearly dictates otherwise.

It is understood that whenever embodiments are described herein with the language "comprising" otherwise analogous embodiments described in terms of "consisting" and/or "consisting essentially of" are also provided.

Those of ordinary skill in the art will understand that various modifications to these preferred embodiments are within the scope of the appended claims. It is the claims and equivalents thereof that define the scope of the present invention, which is not and should not be limited to or limited by this description of certain preferred embodiments.

The invention provides a method of purifying an antibody having (i) a light chain sequence having at least 90% identity with SEQ ID NO:1 and a heavy chain sequence having at least 90% identity with SEQ ID NO:2, or (ii) a light chain sequence having at least 95% identity with SEQ ID NO:1 and a heavy chain sequence having at least 95% identity with SEQ ID NO:2, or (iii) a light chain sequence of SEQ ID NO:1 and a heavy chain sequence of SEQ ID NO:2, In embodiments of the present invention, the antibody is adalimumab. In embodiments of the present invention, the antibody is a biosimilar of adalimumab. In embodiments of the present invention, the antibody has a light chain sequence comprising SEQ ID NO: 3, SEQ ID NO: 5, and SEQ ID NO: 7; and the antibody has a heavy chain sequence comprising SEQ ID NO: 4, SEQ ID NO: 6, and SEQ ID NO: 8. In embodiments of the present invention, the antibody has a light chain sequence comprising SEQ ID NO: 3, wherein Xaa is any naturally occurring amino acid; and has a heavy chain sequence comprising SEQ ID NO: 4, wherein Xaa is any naturally occurring amino acid. In embodiments of the present invention, Xaa of SEQ ID NO: 3 is Threonine or Alanine. In embodiments of the present invention, Xaa of SEQ ID NO: 4 is Tyrosine or Asparagine.

The mammalian cell culture of the method of the present invention may be prepared in any medium suitable for the particular cell being cultured. The medium may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin), trace elements (defined as inorganic compounds usually present at final concentrations in the micromolar range) lipids (such as linoleic or other fatty acids) and glucose or an equivalent energy source. Any other necessary supplements may also be included at appropriate concentrations that would be known to those skilled in the art.

Additional amino acids and nutrients may also be used in accordance with standard cell culture techniques as known to the skilled person, for example to replenish essential amino acids as the cells multiply, replenish an energy source and replenish other essential micronutrients, such as trace elements.

The amount of supplementation required can vary depending on the cellular growth conditions. For example, factors that influence cellular consumption rates, will affect the amount of supplementation that is required to prevent misincorporation. Such factors include, but are not limited to, temperature, osmolality, and pH, as known in the art.

The basal cell culture medium is the medium in which the cell culture is started, prior to any additional supplementation may contain essential amino acids, vitamins (such as folic acid, biotin, and/or thiamine), salts (such as sodium chloride and/or sodium bicarbonate), metal ions (such as, cupric sulphate and/or Ferric ammonium citrate) all foaming agents (such as PLURONIC® (poloxamer)) and an energy source (such as glucose and/or galactose). The particular combination and amounts of each component may vary depending on the cell line, and the recombinant protein to be produced. Any of these salts, polysaccharides, proteins, and lipids, may be removed or reduced by the method of the invention.

The having (i) a light chain sequence having at least 90% identity with SEQ ID NO:1 and a heavy chain sequence having at least 90% identity with SEQ ID NO:2, or (ii) a light chain sequence having at least 95% identity with SEQ ID NO:1 and a heavy chain sequence having at least 95% identity with SEQ ID NO:2, or (iii) a light chain sequence of SEQ ID NO:1 and a heavy chain sequence of SEQ ID NO:2, may be produced by a culture that can be any volume that is appropriate for production of polypeptides. In one embodiment, the volume of the production bioreactor is at least 500 litres. In other preferred embodiments, the volume of the production bioreactor is between 1000 and 15,000 litres, for example 1000, 2000, 2500, 5000, 8000, 10,000, 12,000 or 15,000 litres or more, or any volume in between. As such, the method of purifying the antibody can be used for any titre amount produced by the cell culture. In embodiments of the present invention, the antibody is adalimumab or a biosimilar of adalimumab. In embodiments of the present invention, the antibody has a light chain sequence comprising SEQ ID NO: 3, SEQ ID NO: 5, and SEQ ID NO: 7; and the antibody has a heavy chain sequence comprising SEQ ID NO: 4, SEQ ID NO: 6, and SEQ ID NO: 8. In embodiments of the present invention, the antibody has a light chain sequence comprising SEQ ID NO: 3, wherein Xaa is any naturally occurring amino acid; and has a heavy chain sequence comprising SEQ ID NO: 4, wherein Xaa is any naturally occurring amino acid. In embodiments of the present invention, Xaa of SEQ ID NO: 3 is Threonine or Alanine. In embodiments of the present invention, Xaa of SEQ ID NO: 4 is Tyrosine or Asparagine.

The cells may be maintained until a desired production titre is reached. The cells may be maintained in the subsequent production phase until the titre to the recombinant polypeptide or protein reaches a maximum. In other embodiments, the culture may be harvested prior to this point.

By "impurities" it is meant molecules, ions, and particles that are not desirable in a therapeutic composition comprising the antibody. Such impurities may include polysaccharides, proteins (such as host cell proteins other than the antibody), lipids, ions, and cell debris, aggregates, and fragments of the antibody.

Purifying the antibody from impurities means reducing the amount of at least one impurity in the sample by at least about 10%, 20%, 30%, 40%, 50%, 60%, 70%, 80%, 90% or 100%. This means that the relative amount of the antibody in the sample in comparison to the impurities may increase by about 20%, 30%, 40%, 50%, 75%, 100%, 150%, 200%, or more than 20%.

In an aspect of the present invention, the method of purifying an antibody having (i) a light chain sequence having at least 90% identity with SEQ ID NO:1 and a heavy chain sequence having at least 90% identity with SEQ ID NO:2, or (ii) a light chain sequence having at least 95% identity with SEQ ID NO:1 and a heavy chain sequence having at least 95% identity with SEQ ID NO:2, or (iii) a light chain sequence of SEQ ID NO:1 and a heavy chain sequence of SEQ ID NO:2, from a sample comprising the antibody and impurities, the method comprises contacting the sample with a hydroxyapatite resin under conditions such that the antibody binds to the resin and at least a portion of the impurities do not bind to the resin. In embodiments of the present invention, the antibody is adalimumab or a biosimilar of adalimumab In embodiments of the present invention, the antibody has a light chain sequence comprising SEQ ID NO: 3, SEQ ID NO: 5, and SEQ ID NO: 7; and the antibody has a heavy chain sequence comprising SEQ ID NO: 4, SEQ ID NO: 6, and SEQ ID NO: 8. In embodiments of the present invention, the antibody has a light chain sequence comprising SEQ ID NO: 3, wherein Xaa is any naturally occurring amino acid; and has a heavy chain sequence comprising SEQ ID NO: 4, wherein Xaa is any naturally occurring amino acid. In embodiments of the present invention, Xaa of SEQ ID NO: 3 is Threonine or Alanine. In embodiments of the present invention, Xaa of SEQ ID NO: 4 is Tyrosine or Asparagine.

By "at least a portion", it is meant at least one of the impurities selected from the group consisting of aggregates, fragments, host cell proteins, viral particles, nucleic acids, lipids and polysaccharides is reduced in relative amount in the eluate compared to the amount of that impurity present in the sample.

Hydroxyapatite resin is known in art to be particularly useful for the removal or reduction of aggregates from antibody preparations. Surprisingly, however, the present inventors have found that when used to purify an antibody having (i) a light chain sequence having at least 90% identity with SEQ ID NO:1 and a heavy chain sequence having at least 90% identity with SEQ ID NO:2, or (ii) a light chain sequence having at least 95% identity with SEQ ID NO:1 and a heavy chain sequence having at least 95% identity with SEQ ID NO:2, or (iii) a light chain sequence of SEQ ID NO:1 and a heavy chain sequence of SEQ ID NO:2, the HA chromatography method as set out in the invention is especially effective at removing or reducing fragments (LMW molecules) of the antibody, as well as the expected aggregates (HMW molecules). The yield of recovered the antibodyremains consistently high in the method of the present invention, whilst at the same time enabling the significant reduction of HMW and LMW molecules.

The hydroxyapatite resin may be ceramic hydroxyapatite type I and may have a bead size of 40 μm. The 40 μm resin allows for large scale maintaining up-scale of the process, without any problems with high back pressure which may occur with the 20 μm HA resin, although the 20 μm sizw is often thought to be more selective. Prior to contacting the sample with the hydroxyapatite resin the resin may be pre-equilibrated with a buffer. Preferably the buffer is a sodium phosphate buffer at a pH of between about 6.0 and about 8.0. The pH may be about 6.0, 6.5 7.0, 7.5, or about 8.0. The sodium phosphate may be at a concentration of about 0.2 M to about 1.0 M, the NaPO4 may be at a concentration of about 0.2 M, 0.3 M, 0.4 M, 0.5 M, 0.6 M, 0.7 M, 0.8 M, or 0.9 M; and preferably about 0.5 M.

The contact of the resin with the sample containing the antibody and the impurities may be via a column which has been packed with the resin to a certain bed height. The column may be packed by any method known in the art to a bed height of from approximately about 10 cm to about 20 cm, preferably to about 13±3 cm.

After pre-equilibration, the resin may be equilibrated with at least 10 bed volumes of equilibration buffer. At least about 12, 15, 18, 20, or 25 bed volumes of equilibration buffer may be used. The equilibration buffer may comprise from about 5 mM sodium phosphate ($Na_2PO4$) to about 15 mM sodium phosphate, preferably about 10 mM sodium phosphate. The pH of this buffer may be from about pH 7.0 to about pH 8.0, preferably about pH 7.5.

As known in the art, the ideal pH at which to run a hydroxyapatite column of this type is around pH 8.5 in order to maintain the integrity of the hydroxyapatite. Acceptable selectively for the antibody had been determined during test runs on the resin at pH as low as 6.5. However, bearing in mind the stability of the antibody (at lower pH values) and the fact that hydroxyapatite matrix may begin to degrade at pH levels lower than 7.3 (HA zero charge pH), a pH of about 7.5 was found to be the most effective for the HA equilibration buffer. Therefore, the pH of about 7.5 was determined to be a very satisfactory balance of competing consideration and successfully achieved selectivity and product integrity, as well as maintaining the quality of the resin in order to retain a consistent pressure throughout the process.

The conductivity of the equilibration buffer is preferably about 1.0 mS/cm to about 2.0 mS/cm, preferably about 1.5 mS/cm.

After the equilibration step, the sample containing the antibody and impurities is contacted with the column under conditions such that the the antibody binds to the resin. The conditions may comprise the adjustment of the sample to about 5 mM of sodium phosphate, by using a pre-equilibration buffer, if necessary. A suitable pre-equilibration buffer may comprise acetic acid a concentration of which approximately 1 M, may be used to reduce the pH to about pH 7.5. Any other acid and/or concentration may be used, as will be known by the skilled person.

The sample may be the supernatant obtained directly after cell culture clarification (for example centrifugation to remove of cell debris) to leave the cell culture medium containing the secreted antibody. Alternatively, the sample may be the result of previous purification methods, including but not limited to one or more of Protein A chromatography, viral inactivation, cation exchange chromatography, nanofiltration, anionic exchange chromatography, and/or ultrafiltration.

HA chromatography relies on a number of non-specific associations between a particular molecule and the resin matrix, and therefore conditions for any particular protein cannot be readily predicted. Therefore, buffer concentrations and pH values are not standard when purifying different types of protein and, in fact, can vary hugely from molecule to molecule.

Preferably, the pH adjusted (if necessary) sample is loaded onto the equilibrated column to achieve a flow rate of about 200 to about 300 cm/hour, preferably about 250 cm/hour, or a rate that results in a retention time (the period of time that the sample spends in the column) of about 2, about 3, about 4 or about 5 minutes, preferably about 3.6 minutes. The sample should be loaded such that about 25 to about 40 g of the antibody per litre of resin contacts the resin, such as 25 mg, 30 mg, 35 mg or 40 mg. Preferably, no more than about 32 g of the antibody per litre of resin is loaded on to the column. As explained below, it was surprisingly found that reducing the load of the antibody, increased the reduction of the level of fragments when using the HA chromatography. Increasing the protein load may result in more binding of the aggregates (HMW) or fragments (LMW) to the resin, due to the density of these materials on the column/resin. This is clearly undesirable as these HMW and LMW products may then be eluted along with the the antibody in the final step.

Methods for determining the concentration of an antibody in a sample are known in the art, including a Biuret test, spectrophotometry at a wavelength of 280 nm, and other protein assays.

The method of the invention further comprises washing the resin with a wash buffer under conditions such that at least portions of the unbound impurities are washed from the resin/through the column and therefore, separated from the bound antibody. Such conditions may include washing the column with the equilibration buffer, as defined above. At least 5, 6, 7, 8, or 9 bed volumes of the equilibration buffer may be applied. At least 10 bed volumes of equilibration buffer may be applied in the wash step, (b). The final amount of post load wash (equilibration buffer) applied is at least 5 Column volumes.

The wash buffer may be applied until, for example, the $UV_{280\ nm}$ reading of fractions obtained from the wash flow through returns to a pre-determined baseline level, indicating that no further detectable unbound impurities remain within the column, that is at least a portion of the impurities have been separated from the antibody. Any other suitable method of measuring impurities in each fraction may be employed, provided that baseline levels can be determined.

The flow-through of the wash step (b) that is collected after applying the wash buffer to the column and which contains any impurities that are carried with it may be collected in regular fractions, and the impurity content of each fraction may be analysed to determine whether different impurities are washed through at different times and also to determine when all detectable unbound impurities have been cleared. When all detectable unbound impurities have been cleared the fraction returns to baseline levels as determined by whichever measuring method is being utilised. Different methods may be used for the detection of different impurities.

The method of the invention further comprises eluting the antibody from the resin under conditions such that the antibody becomes unbound from the resin and is collected as an eluate, and such that the eluate has a lower level of impurities than the sample of step (a). That is to say, the antibody has been purified from at least a portion of the impurities.

The elution is carried out by way of the application of an elution buffer. The elution buffer may comprise about 5 mM, about 10 mM, or about 15 mM sodium phosphate; about 300, about 350 mM, or about 400 mM sodium chloride (NaCl); and be at a pH of about pH 7.0, about 7.5, or about pH 8.0. Preferably, the elution buffer comprises about 10 mM sodium phosphate, about 350 mM sodium chloride, and is at about pH 7.5. No more than about 10 bed volumes of elution buffer may be used, in order to prevent the over dilution of the antibody or the release of any impurities from the column. Preferably, no more than 5, 6, 7, 8, or 9 bed volumes are used.

Again, the elution may be collected in fractions to determine when the maximum yield of the antibody has been eluted from the resin. The point at which all of the bound antibody has been eluted may be determined by a return to baseline measurement by a method known in the art.

In the method of the present invention, each step may be performed at about 15 to 25° C., preferably 18° C. to about 22° C. Each step may be performed at a linear flow rate of about 200 cm/hr to about 300 cm/hr, preferably at about 250 cm/hr, or any rate that enables steady transition of the sample through the column and a retention time of about 2-5 minutes, preferably about 3.5 minutes. Each step may be performed at a pressure of no more than about 4.0 bars, no more than about 3.5 bars, or no more than about 3.0 bars.

The hydroxyapatite resin may be CHT ceramic hydroxyapatite Type I, 40 μm, (BioRad, Hercules, California) or equivalents thereof.

The removal of impurities can be tested by various ways known in the art, i.e. the presence or absence (or change in level) of proteins, nucleic acids, lipids, polysaccharides, and fragments and aggregates of the antibody, including spectroscopy or Biacore SPR (Surface Plasmon Resonance) assays.

EXAMPLES

Example 1

An initial experiment was carried out with HA resin to determine its suitability for HMW (aggregates) and LMW (fragments) removal, and thus whether it could be used in purification methods of the antibody, and in particular a biosimilar of adalimumab.

Hydroxyapatite type I, 20 μm was initially used to check its capability for LMW and HMW removal. The 20 μm bead size resin is generally not the recommended media for manufacturing processes. However, it gives the good selectivity, which is ideal for early experiments to determine good binding, washing and eluting conditions, as well as load and flow rate. For initial experiments, the pH was set to 6.5, allowing a better selectivity.

Figure 1A:
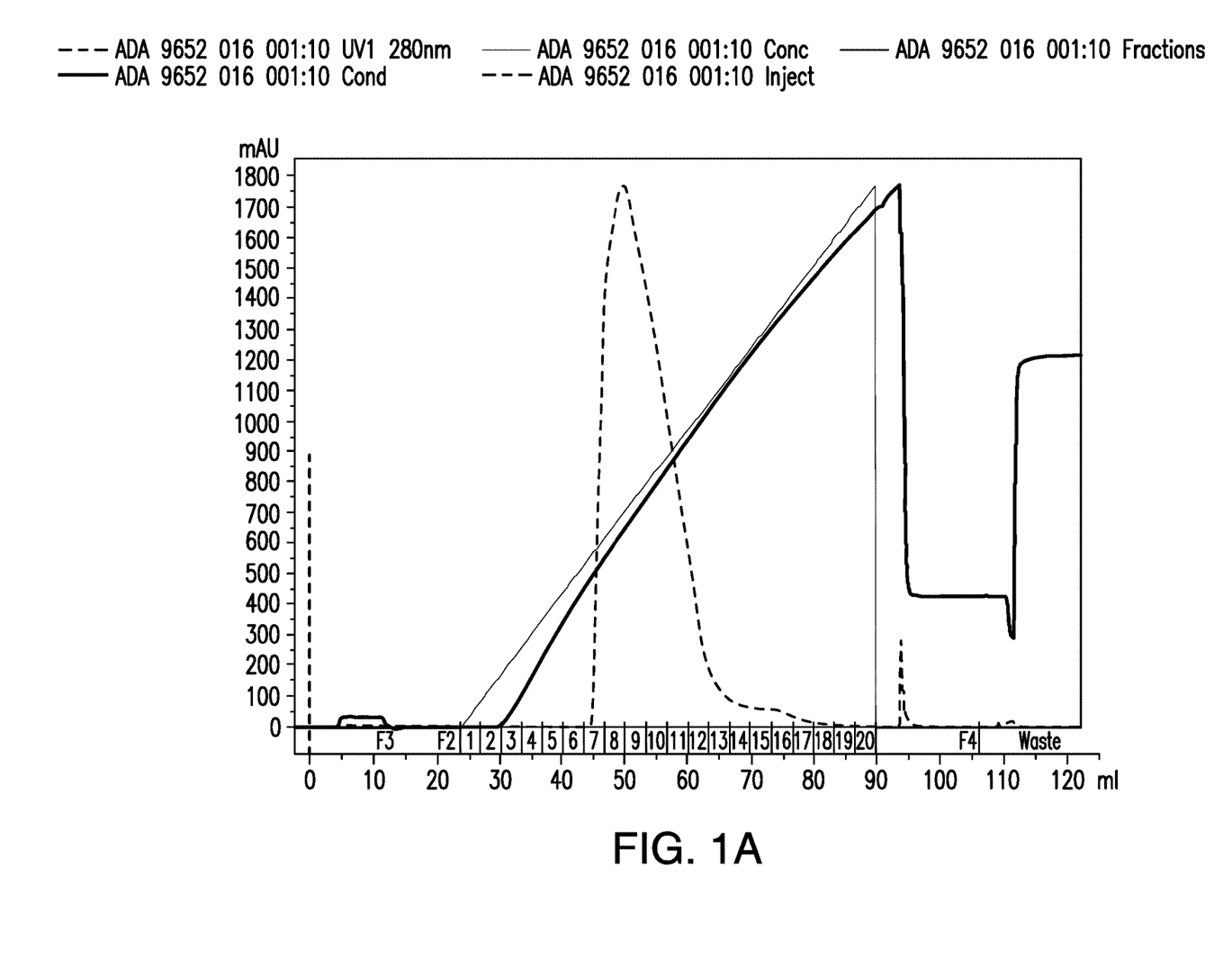
FIG. 1A shows the chromatic profile of the initial feasibility experiment using HA type 1, 20 µm NaCl gradient experiment at pH 6.5. Load pH 6.5 with 5 mM NaPO4, elution 0 to 2 M NaCl with 10 mM NaPO4, and stripping with 0.5 M NaPO4 pH 6.5.

Intermediate bulk of the antibody, and in this case the biosimilar of adalimumab was loaded onto the HA resin at a capacity of 25 g/L after adjustment to a final phosphate concentration of 5 mM with a 0.5 M sodium phosphate solution and to a pH 6.5 with 1 M Tris base. After a post load wash step with the equilibration buffer, a gradient elution with NaCl 2 M was applied. The chromatographic profile at 280 nm clearly showed two elution peaks, with a main peak at the beginning of the NaCl gradient and a second small shoulder eluting later. FIG. 1A shows the chromatographic profile obtained for this experiment.

Figure 1B:
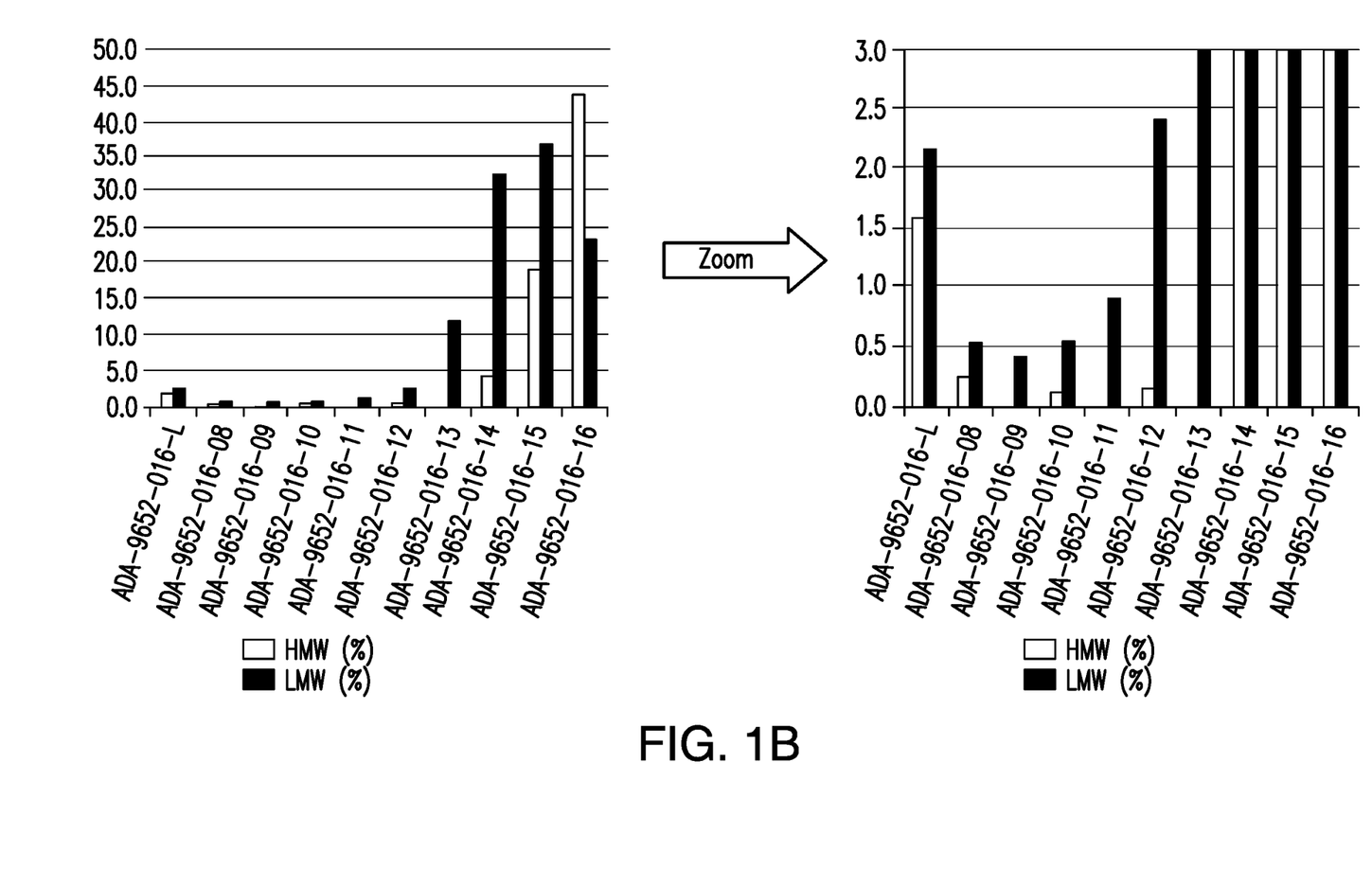
FIG. 1B shows the aggregate (HMW) and fragment (LMW) clearance using HA Type I, 20 µm NaCl gradient experiment at pH 6.5. HMW results by SE-HPLC and LMW by Caliper under non-reducing conditions.

FIG. 1B shows the evolution of the HMW and LMW content measured in the fractionated peaks. Fractions 08 to 13 had HMW levels lower than in the load material, whereas the fractions 14 to 16 were enriched. LMW were reduced in fractions 08 to 11 while the fractions 12 to 16 were enriched.

The HA Type I, 20 μm media showed high selectivity potential for both HMW and LMW, which were eluted after the product of interest in a NaCl gradient. The tested conditions were successful in terms of HMW and LMW removal but were not ideal for the manufacturing scale. Indeed, hydroxyapatite resin is very sensitive to acidic pH conditions with visible degradation of the resin bead at a pH lower than 7.3. Furthermore, the resin HA Type I with 20 μm bead size is subjected to high backpressure even at low flow rates. Hence, the next development steps were focused on testing the selectivity of a HA type I, 40 μm resin and its capability at higher pH values (ideally >7.4)

Example 2

A preliminary test to evaluate the selectivity of the hydroxyapatite type I matrix with an average bead size of 40 μm was first performed at pH 6.5

Figure 2:
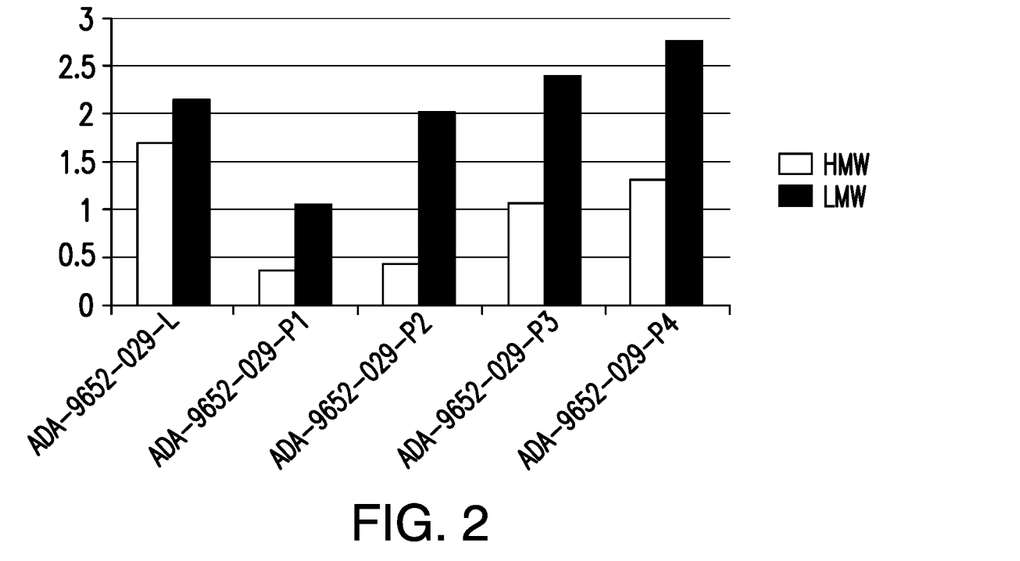
FIG. 2 shows the HMW and LMW clearance using HA type 1, 40 µm NaCl steps experiment at pH 6.5; HMW and LMW were measured by SE-HPLC and Caliper under non-reducing conditions.

Aggregate levels were lower in all tested pools compared to the load material. However, the target for HMW was obtained only for the first two representative pools P1 and P2. LMW were also reduced in both representative pools but the target was reached only in the first pool P1. The results for LMW and HMW are shown in FIG. 2.

This experiment showed the feasibility to perform the HA purification using an average bead size suitable for the manufacturing scale.

Example 3

Figure 3:
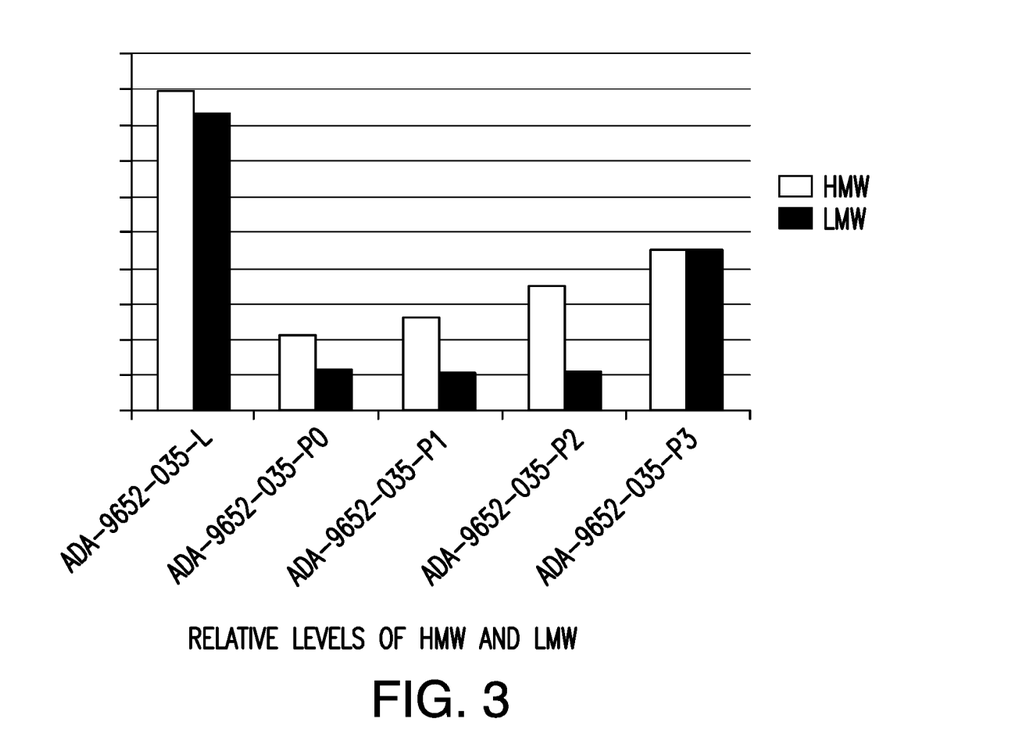
FIG. 3 shows the HMW and LMW clearance using HA Type I, 40 µm NaCl gradient experiment at pH 7.5; HMW results by SE-HPLC and LMW by Caliper under non-reducing conditions.

In a second experiment, pH values higher than 6.5 were tested as well. A first run was performed at pH 7.5 with a linear sodium chloride elution gradient and representative pools were tested for LMW and HMW content. A pH of 7.5 was chosen as a compromise between stability of the antibody, and in this case the biosimilar of adalimumab (highest at pH 5.0) and HA resin integrity (which degrades below pH 7.3). The results for LMW and HMW are shown in FIG. 3.

All representative pools tested showed reduced LMW and HMW levels compared to the load material and the HMW target was reached in pools P0 to P2.

This experiment showed the feasibility to perform the HA purification at a higher pH to render it suitable for the manufacturing scale.

Example 4

Figure 4:
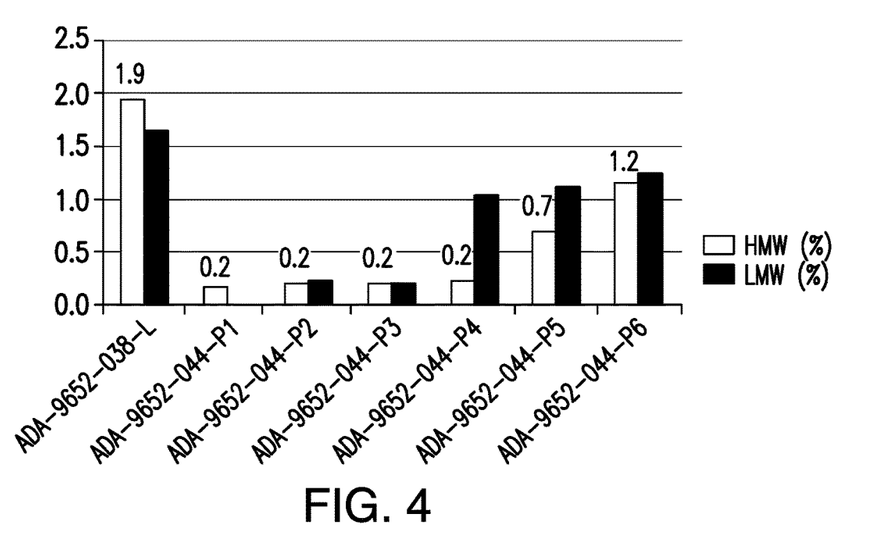
FIG. 4 shows the HMW and LMW clearance using HA Type I, 40 µm NaCl steps experiment at pH 7.5; HMW results by SE-HPLC and LMW by Caliper under non-reducing conditions.

The replacement of the initial linear salt gradient elution with a more suitable step gradient elution was also assessed because linear gradient elution is not suitable in manufacturing.

LMW and HMW levels in the pools are reported in FIG. 4 and it can be seen that the HMW levels from pools P1 to P4 reached the target level while the LMW content showed a significant increase in pool P4 and the following. Based on these results, an elution sodium chloride concentration corresponding to the last step of pool 3 or 4 was used going forward, (300 to 400 mM NaCl). The final sodium chloride concentration was later confirmed by a single step elution test as described in Example 6.

Example 5

The dynamic binding capacity of the HA Type I, 40 μm resin was assessed by determining the 5% fraction of the break through curve (BTC 5%). The 80% reaction of the obtained BTC 5% equalled 42 g of the biosimilar of adalimumab per litre of resin.

Example 6

Figure 5:
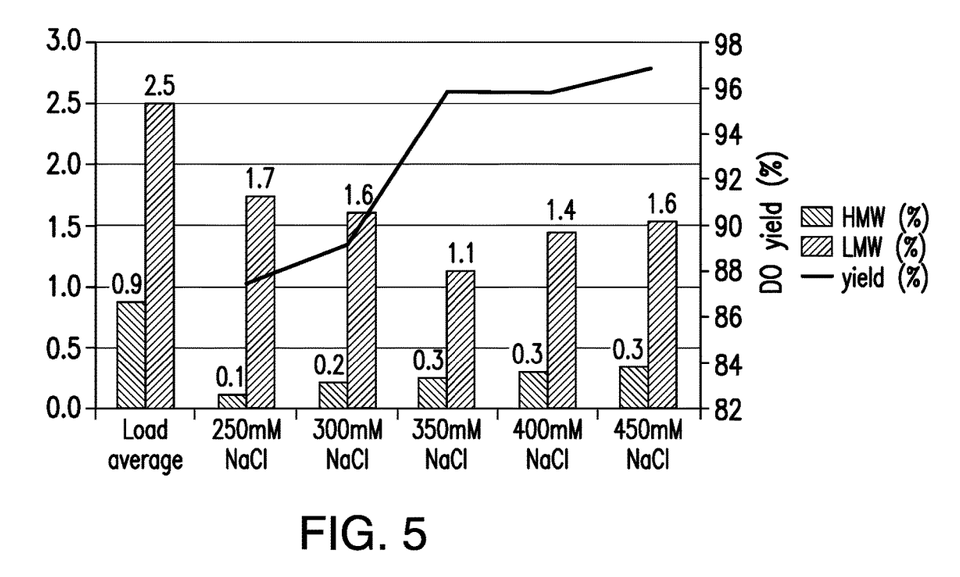
FIG. 5 shows the HMW and LMW clearance and yield using HA Type I, 40 µm NaCl step gradient elution experiment at pH 7.5. 5 different runs were performed using 5 different elution conditions; HMW results by SE-HPLC, LMW by Caliper under non-reducing conditions, and step yield by DO 280 nm.

A series of runs was performed to determine the optimal sodium chloride concentration for the elution condition at pH 7.5. All runs were performed at a DBC of 42 g/L. A limit of not more than 10 elution bed volumes was used to prevent large volumes at manufacturing scale. Each elution fraction was tested for LMW, HMW content and recovery of the biosimilar of adalimumab. The obtained results are shown in FIG. 5.

As expected, higher recovery was observed for the higher sodium chloride concentration. For all tested conditions, HMW results were within the specification. The LMW levels were lower than in the load material but higher than expected. In fact, in the previous experiments such high LMW content was not observed and it was thought to be linked to the higher DBC used in this run (42 versus 25 g/L).

The elution condition of 350 mM sodium chloride was nevertheless chosen as a best compromise between the HMW, LMW content and product recovery.

Example 7

Figure 6:
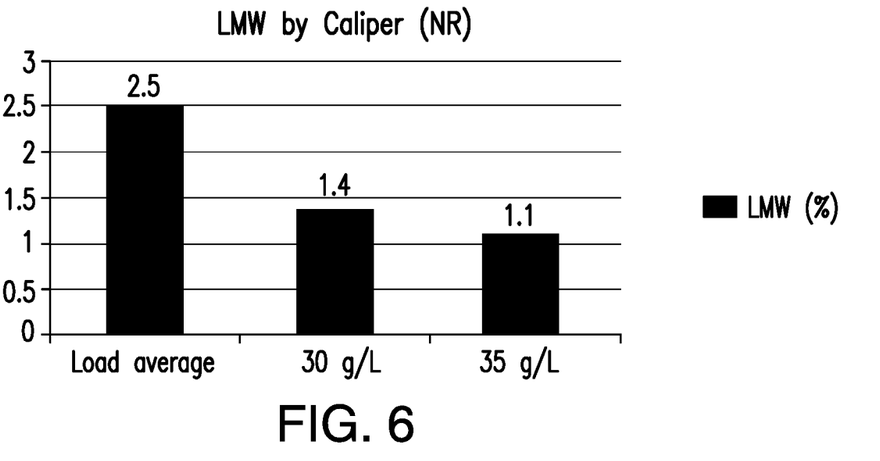
FIG. 6 shows LMW reduction using HA eluate fraction LMW content by Caliper under non-reducing conditions.

Additional runs at 30 and 35 g/L were performed to determine whether a lower DBC can increase the LMW clearance. Both tested conditions allowed the LMW target to be reached. The observed difference in LMW content between the two DBC concentrations (FIG. 6) were within the analytical variability of the method (i.e. 25% CV for n=65) and, thus, not significant.

A final capacity of NMT 32 g/L was chosen to ensure a final level of LMW within the targets.

Example 8

Figure 7:
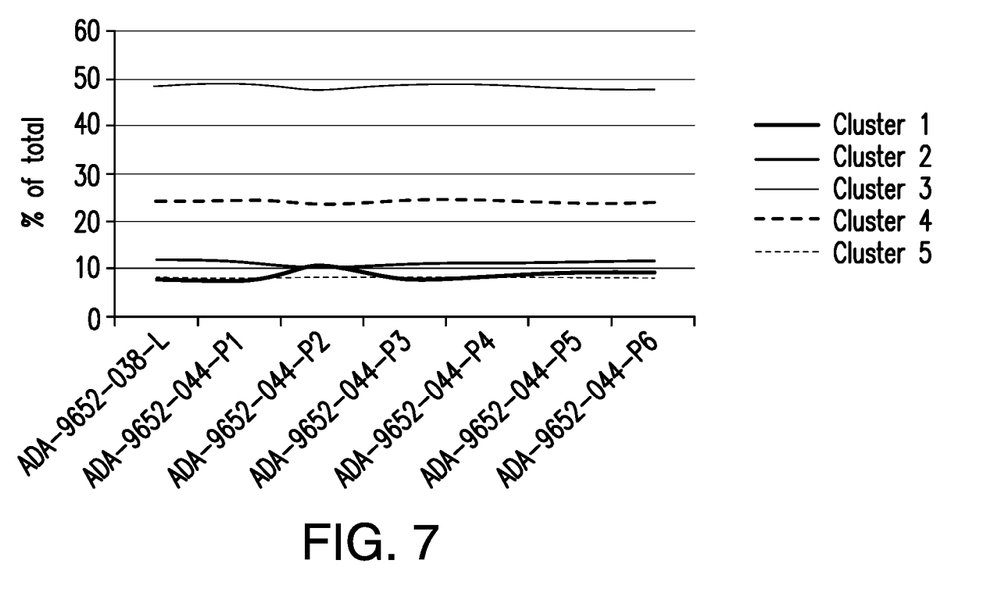
FIG. 7 shows the evolution of charged forms during elution using HA Type I, 40 µm NaCl steps experiment at pH 7.5. Charge profile results by iCE (Imaged capillary isoelectric focusing).

The evolution of the charged forms during elution was also monitored as reported in FIG. 7 and no significant impact was observed on this quality attribute.

The invention claimed is:

1. A method of purifying an antibody having a light chain sequence comprising SEQ ID NO:1 and a heavy chain sequence comprising SEQ ID NO:2 from a sample comprising the antibody and impurities, the method comprising:

(a) contacting the sample with a hydroxyapatite resin under conditions such that about 25 mg to about 40 mg of the antibody per liter of resin binds to the resin and at least a portion of the impurities remain unbound to the resin, wherein the conditions such that the antibody binds to the resin comprise the use of a loading buffer, wherein the loading buffer: (i) has a pH of about pH 7.5; and (ii) comprises about 5 mM NaPO$_4$;

(b) washing the resin with a wash buffer under conditions such that at least a portion of the impurities are separated from the antibody; and (c) eluting the antibody from the resin under conditions such that the antibody becomes unbound from the resin to produce an eluate wherein the eluate contains a lower level of impurities than the sample of step (a), wherein the conditions such that the antibody becomes unbound from the resin comprise the use of an elution buffer, wherein the elution buffer: (i) has a pH of about pH 7.5; (ii) comprises about 10 mM $NaPO_4$; and (iii) comprises about 350 mM NaCl, wherein about means within 3% of the given value.

2. The method of claim 1, wherein the antibody is adalimumab or a biosimilar of adalimumab.

3. The method of claim 1, wherein the impurities comprise one or more of host cell proteins, nucleic acid molecules, lipids, polysaccharides.

4. The method of claim 1, wherein the impurities comprise aggregates of the antibody or fragments of adalimumab or mixtures thereof.

5. The method of claim 1, wherein about 25 mg to about 35 mg of the antibody per litre of resin binds to the resin in step (a).

6. The method of claim 4, wherein about 32 mg of the antibody per litre of resin is contacted with the resin.

7. The method of claim 1, wherein the hydroxyapatite resin is ceramic hydroxyapatite, type I, 40 μm.

8. The method of claim 1, where the resin has a bed height from about 10 cm to about 16 cm.

9. The method according to claim 1, wherein the method is carried out at about 15-25° C.

10. The method according to claim 1, wherein the eluate of step c) comprises aggregates at a level of at least 75% lower than the level of aggregates in the sample of step (a).

11. The method according to claim 1, wherein the eluate of step (c) comprises fragments at a level of at least 70% lower than the sample of step (a).

12. A method of producing an antibody having (i) a light chain sequence comprising SEQ ID NO:1 and a heavy chain sequence comprising SEQ ID NO:2 comprising the steps of:

(a) expressing the antibody in CHO cells and secreting the antibody into a cell culture media to obtain a sample;

(b) contacting the antibody with a hydroxyapatite resin under conditions such that about 25 mg to about 40 mg of the antibody per liter of resin binds to the resin and at least a portion of the impurities remain unbound to the resin, wherein the conditions such that the antibody binds to the resin comprise the use of a loading buffer, wherein the loading buffer: (i) has a pH of about pH 7.5; and (ii) comprises about 5 mM $NaPO_4$;

(c) washing the resin with a wash buffer under conditions such that at least a portion of the impurities are separated from the antibody; and (d) eluting the antibody from the resin under conditions such that the antibody becomes unbound from the resin to produce an eluate, wherein the eluate contains a lower level of impurities than the sample of step (a), wherein the conditions such that the antibody becomes unbound from the resin comprise the use of an elution buffer, wherein the elution buffer: (i) has a pH of about pH 7.5; (ii) comprises about 10 mM $NaPO_4$; and (iii) comprises about 350 mM NaCl, wherein about means within 3% of the given value.

13. The method of claim 12, wherein the antibody is adalimumab or a biosimilar of adalimumab.

* * * * *